US 9,375,663 B2

(12) United States Patent
MacKay Pett

(10) Patent No.: US 9,375,663 B2
(45) Date of Patent: Jun. 28, 2016

(54) SANITIZATION AND REGENERATION OF POROUS FILTER MEDIA WITH OZONE IN BACKWASH

(71) Applicant: Ozono Polaris, S.A. de C.V., Puebla (MX)

(72) Inventor: David Ross MacKay Pett, Puebla (MX)

(73) Assignee: Ozono Polaris, S.A. de C.V., Puebla (MX)

(*) Notice: Subject to any disclaimer, the term of this patent is extended or adjusted under 35 U.S.C. 154(b) by 0 days.

(21) Appl. No.: 14/727,567

(22) Filed: Jun. 1, 2015

(65) Prior Publication Data

US 2015/0343336 A1  Dec. 3, 2015

Related U.S. Application Data

(60) Provisional application No. 62/005,568, filed on May 30, 2014.

(51) Int. Cl.
| | |
|---|---|
| *B01D 15/00* | (2006.01) |
| *B01D 24/46* | (2006.01) |
| *B01D 29/68* | (2006.01) |
| *B01J 20/20* | (2006.01) |
| *B01J 20/34* | (2006.01) |
| *C02F 1/28* | (2006.01) |
| *C02F 1/78* | (2006.01) |

(52) U.S. Cl.
CPC .......... *B01D 24/4636* (2013.01); *B01D 29/68* (2013.01); *B01J 20/20* (2013.01); *B01J 20/3475* (2013.01); *C02F 1/281* (2013.01); *C02F 1/78* (2013.01); *C02F 1/283* (2013.01); *C02F 2303/04* (2013.01); *C02F 2303/16* (2013.01)

(58) Field of Classification Search
CPC . B01D 24/46; B01D 24/4631; B01D 24/4636
USPC ........................................................ 422/280
See application file for complete search history.

(56) References Cited

U.S. PATENT DOCUMENTS

| | | | |
|---|---|---|---|
| 3,927,175 A | | 12/1975 | Garofano et al. |
| 3,932,278 A | * | 1/1976 | Meidl .................... B01D 23/24 134/25.5 |
| 4,080,287 A | | 3/1978 | Conway et al. |
| 4,694,179 A | | 9/1987 | Lew et al. |
| 4,766,321 A | | 8/1988 | Lew et al. |
| 4,786,418 A | | 11/1988 | Garg et al. |
| 4,792,407 A | | 12/1988 | Zeff et al. |
| 4,861,484 A | | 8/1989 | Lichtin et al. |
| 4,959,142 A | | 9/1990 | Dempo |
| 5,190,659 A | | 3/1993 | Wang et al. |
| 5,236,595 A | | 8/1993 | Wang et al. |
| 5,244,585 A | | 9/1993 | Sugimoto |

(Continued)

FOREIGN PATENT DOCUMENTS

EP         1038840 A2     9/2000

OTHER PUBLICATIONS

International Search Report issued in PCT/IB15/54158, mailed Oct. 16, 2015.

*Primary Examiner* — Kevin Joyner
(74) *Attorney, Agent, or Firm* — Heslin Rothenberg Farley & Mesiti P.C.

(57) ABSTRACT

The invention provides methods and systems for sanitizing and/or regenerating porous filter media using dissolved ozone in the filter backwash under fluidized conditions.

19 Claims, 6 Drawing Sheets

(56) References Cited

U.S. PATENT DOCUMENTS

| | | |
|---|---|---|
| 5,256,299 A | 10/1993 | Wang et al. |
| 5,403,480 A | 4/1995 | Sugimoto |
| 5,466,367 A | 11/1995 | Coate et al. |
| 5,707,528 A | 1/1998 | Berry |
| 5,756,054 A | 5/1998 | Wong et al. |
| 5,756,721 A | 5/1998 | Eden et al. |
| 5,882,588 A | 3/1999 | Laberge |
| 5,897,832 A * | 4/1999 | Porter ............... A61L 2/183 422/28 |
| 5,904,832 A | 5/1999 | Clifford et al. |
| 5,928,516 A | 7/1999 | Hopkins et al. |
| 6,027,642 A | 2/2000 | Prince et al. |
| 6,245,242 B1 | 6/2001 | Schuster et al. |
| 6,673,248 B2 | 1/2004 | Chowdhury |
| 7,037,871 B1 | 5/2006 | Galperin et al. |
| 7,267,710 B2 | 9/2007 | Tatsuhara et al. |
| 8,293,669 B2 | 10/2012 | Kirkpatrick |
| 8,318,027 B2 | 11/2012 | McGuire et al. |
| 2008/0032010 A1 * | 2/2008 | Hankinson ............. A23B 7/015 426/248 |
| 2009/0261042 A1 | 10/2009 | Semiat et al. |
| 2010/0292844 A1 | 11/2010 | Wolf |
| 2011/0042236 A1 | 2/2011 | Kim et al. |
| 2013/0220913 A1 * | 8/2013 | Cohen ................ B01D 24/002 210/275 |

* cited by examiner

SANITIZATION AND REGENERATION OF POROUS FILTER MEDIA WITH OZONE IN BACKWASH

CROSS REFERENCE TO RELATED APPLICATION

This application claims priority to U.S. Provisional Application No. 62/005,568, filed on May 30, 2014, the entire contents of which are hereby incorporated herein by reference.

BACKGROUND

This invention relates to a new and improved method of sanitizing, and simultaneously regenerating, backwashable, packed or fixed bed adsorption filters formed of porous media or materials which are typically employed during the purification of municipal or industrial water and wastewater streams. More specifically, the invention relates to sanitizing and regenerating porous particles comprising activated carbon that are exhausted by the proliferation of microorganisms, organics and/or other contaminants.

Examples of porous filter media include granular activated carbon (or "GAC") or pelletized activated carbon, activated alumina, zeolite and synthetic magnesium silicate. Porous filter media such as granular activated carbon is widely used in water treatment systems to filter organic material, and to improve taste and odor. Activated carbon is also used in air treatment systems to remove volatile organic carbon (VOC). Depending on the water to be treated, GAC fixed bed adsorption filters may be used in combination (i.e. in sequence) with a primary filtration bed comprised of a different filter media (e.g. sand or other dual, or "mixed," filter media).

Activated carbon is one of the most powerful adsorbents. It has a high internal porosity, and hence a large internal surface area (i.e. 500-1500 $m^2/g$). As such, it has the ability to remove a large variety and wide range of compounds from contaminated waters and/or air, including organics. This makes it one of the most effective media for removing a wide range of contaminants from surface water, industrial and municipal waste waters, landfill leachate and contaminated groundwater, which has led to its increased use for water treatment. Adsorption is particularly effective in treating low concentration waste streams and in meeting stringent treatment levels.

One limitation in the use of granular activated carbon to filter water, however, is that it provides a breeding ground for bacterial growth when the activated carbon is used to remove organic contaminants as this adsorbed organic material is used as food for the bacteria. In addition, GAC deteriorates residual disinfectants, such as chlorine and ozone, by chemical reduction.

These two factors can lead to excessive bacterial growth in a filter bed when microbes are present, which can in turn lead to serious problems with either the treatment system (i.e. increased head loss across the filter, more frequent backwashing or "down time", etc) or with the filtered, or treated effluent stream (presence of opportunistic pathogens, unwanted taste and odors, increased turbidity, etc.).

Bacterial growth, therefore, in activated carbon filter media used for the removal of organic contaminants in water can be a serious problem. To avoid bacterial growth requires periodic sanitization of the filter to control growth and the resulting contamination of the filtered effluent stream. For example, weekly sanitization cycles of up to 24 hours are often required. Sanitization is usually done with steam, with significant carbon loss, or chemicals (e.g. caustic soda), which requires extensive rinsing. Both of these processes require having the filter out of service for many hours, are costly in terms of capital investment and energy consumption, and have a negative environmental impact. Furthermore, these conventional sanitization processes often give limited, if any, restoration, or recuperation, of the carbon's adsorptive capacity ("regeneration"), as discussed below.

Another limitation in the use of activated carbon for filtering water of any type (e.g. wastewater, industrial process water, surface water, drinking water, groundwater, etc.) is the exhaustion of the carbon's adsorptive capacity over time, which in turn interferes with the filter's ability to function. After a period of filtration, the pores of the porous media particles begin to accumulate contaminants (or impurities) that can inhibit the filter's operation. These contaminants can be biological (i.e. viruses, bacteria, protozoans, and other microorganisms) or non-biological, (organics, chlorine, arsenic), and because they are adsorbed, they cannot be removed by conventional backwashing (which removes loose particles contained within the filter bed). The adsorbed materials fill the pores and cover the surface of the porous carbon particles contained within the filter, which decreases or "exhausts" the adsorption capacity of the carbon and results in reduced filter performance (e.g. higher backwash frequency, reduced flow-rates, increased water turbidity, breakthrough of contaminants or a combination thereof). Therefore, periodic replacement or regeneration, either onsite or off-site, of the carbon is required.

Activated carbon is an expensive filter media, and in many cases, the cost of replacing saturated (or "spent") carbon is too expensive for its use to be economically feasible. The cost depends on how frequent carbon replacement is required, which is related to the contaminant load within the water stream. There is an additional cost to replacement because it can require significant filter downtime and labor, and it may not be possible for water treatment systems that only have one filtration bed. As an alternative to full replacement, the exhausted carbon can be regenerated either onsite or off site to restore the adsorptive capacity of spent activated carbon by desorbing, or removing, adsorbed contaminants.

Several methods exist for the regeneration of spent activated carbon:

Thermal Regeneration. This is the most common technique employed in industrial processes to regenerate activated carbon. Using this process the activated carbon is heated to a specified temperature, which then burns off the adsorbed organic contaminants. This is a widely used method and regenerates the carbon very well, but it has disadvantages. First, thermal regeneration causes high carbon losses. Second, because it requires high temperatures, it requires a considerable capital expense for a high energy roasting furnace, and the process is an environmentally and financially expensive process. Water treatment plants that use thermal regeneration, therefore, must be large enough to make it economically viable for regeneration to occur onsite. For smaller treatment plants, it is more common to ship spent activated carbon to a specialized regeneration facility. However, this requires unpacking the filter, transporting it to a facility (often times remotely located), returning the carbon to the plant, and repacking the filter. As with replacement, thermal regeneration has the additional cost associated with filter downtime.

Steam Regeneration/Sanitization. This method can be employed on its own or in combination with thermal regeneration. On its own, this method is limited to regenerating carbon which has retained only a few, highly volatile, contaminants. Furthermore, in practice, cooling the carbon after steam sanitization tends to fracture the carbon granules producing fines. This causes carbon loss and requires expensive polishing filters positioned immediately after the carbon filters, wherein the polishing filters need to be replaced every few weeks.

Alternative Methods. Alternative methods of regenerating and sanitizing activated carbon are needed due to the high cost, environmental impact and limitations of conventional methods. Known alternative regeneration and sanitization methods include: chemical and solvent regeneration; electrochemical regeneration; ultrasonic regeneration; and wet air oxidation. Many of these methods, if not all, have not yet been applied on an industrial scale.

Thus, a need exists for improved methods for the sanitization and/or regeneration of granular porous filter media, such as GAC. More specifically, there is an unfilled need for improved, on-site sanitization methods that are faster; simple; have lower energy costs; have reduced environmental impact; are easier to implement in situ (or "in place") without the need to unpack a filter bed and transport the carbon to an off-site facility; and result in sanitization and regeneration at a level acceptable on an industrial scale.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

In this specification, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The present invention satisfies the need for improved methods for the sanitization and/or regeneration of granular porous filter media, such as GAC. The present invention may address one or more of the problems and deficiencies of the art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

Attempting to sanitize porous filter media, such as GAC, with ozonated water has been limited by the fact that the carbon destroys the ozone so it cannot reach deep into the static filter bed. Attempting to sanitize GAC with gaseous ozone has been limited by deterioration of the carbon particles. The present invention solves one or more of the deficiencies in the art by utilizing ozonated backwash water for the sanitization and/or regeneration of a fluidized bed, for example, granular activated carbon.

The invention relates to the use of dissolved ozone in the backwash water stream to sanitize and/or regenerate porous filter media by allowing the filter bed to expand and fluidize during a backwash cycle so that every particle (or granule) contacts with the ozone each time the particles near the location of the filter where the backwash feed stream is being introduced into the filter bed that is being fluidized. By way of further example, when cleaning a porous media filter bed becomes necessary, backwashing is typically employed whereby water is forced upward through the porous media bed. The upward flow of water through the granular filter bed causes the porous particles to fluidize, or become suspended in the fluid flow, when sufficiently high flow rates are employed. At least partial fluidization of the particles contained within a filter bed is commonly achieved during a backwashing cycle.

Accordingly, an object of this invention is to provide a novel, improved one-step method of simultaneously sanitizing and regenerating activated carbon, or other insoluble porous particles (i.e. activated alumina, zeolite and synthetic magnesium silicate), to enhance the adsorptive capacity thereof and allow reuse within a filter bed without any substantial loss of downtime for the treatment system. The method disclosed herein is simple, cost efficient and highly effective, and prolongs the operating time ("life") of fixed-bed filters by allowing one to either completely, substantially or partially eliminate bacteria that is present in the filter media to avoid uncontrolled growth thereof, while simultaneously either completely, substantially or partially regenerating the adsorptive capacity of the filter media.

More particularly, embodiments of the present invention provide an improvement in a water treatment method for sanitizing a fixed bed of porous filter media employed in treating a water stream, wherein said fixed bed has a first flow direction during filtration, comprising the steps of mixing ozone with at least a portion of a water stream to produce an ozonated feed stream comprising a dissolved ozone solution; introducing the dissolved ozone solution into said fixed bed at a second flow direction substantially different from the first flow direction; contacting the porous filter media with the dissolved ozone solution for a predetermined time and in a concentration sufficient to sanitize said filter media; and conducting said contacting step at a predetermined minimum fluidization velocity for the filter media.

Still other embodiments provide a sanitization method with a dissolved ozone solution comprising about 0.5 mg/L to about 12 mg/L residual dissolved ozone when introduced into the fixed bed.

Still other embodiments provide a method of simultaneously sanitizing and regenerating a fixed bed filter containing porous particles and employed in filtering a water stream, wherein said fixed bed comprises a first flow direction during filtration, said method comprising the steps of: mixing ozone with a portion of a purified water stream to produce a dissolved ozone solution; initiating a backwash cycle by introducing the dissolved ozone solution into said fixed bed at a second flow direction opposite to that of the first flow direction; filling said fixed bed with the dissolved ozone solution at a minimum flow rate sufficient to expand the fixed bed and create a fluidized bed, thereby agitating the particles contained within the fluidized bed and allowing the ozone to directly and repeatedly contact the porous particles with the dissolved ozone solution as the only active treatment chemical; and discontinuing contacting said porous particles with the dissolved ozone solution.

Embodiments also include a system for simultaneously sanitizing and regenerating exhausted activated carbon, comprising a vessel containing a fixed bed of porous filter media with a first flow direction for filtration; an ozone generator for producing ozone; a first backwash stream comprising purified water with a second flow direction different from said first flow direction; an ozone injector device operationally configured to inject ozone into at least a portion of said first backwash stream to produce an ozonated backwash stream with a predetermined residual ozone concentration; and a waste drain for disposal of and discharging backwash effluent from said fluidized bed, wherein said backwash effluent is depleted of dissolved ozone, wherein said system is configured to turn from a filtration mode to a backwash mode for backwashing said filter bed at the second flow direction using the ozonated backwash stream and at a minimum fluidization velocity sufficient to convert the fixed bed to a fluidized bed. The sanitization system may be operationally configured to retrofit an existing water treatment system.

Further objectives are to provide an in situ method that offers an economical alternative to filter media replacement or conventional regeneration methods; that does not require filter shut-down for a substantial, extended length of time; that does not require rinsing or washing of the filter media contained within a filtration bed following the sanitization treatment; and/or that does not produce contaminated backwash effluent.

DETAILED DESCRIPTION

Figure 1A:
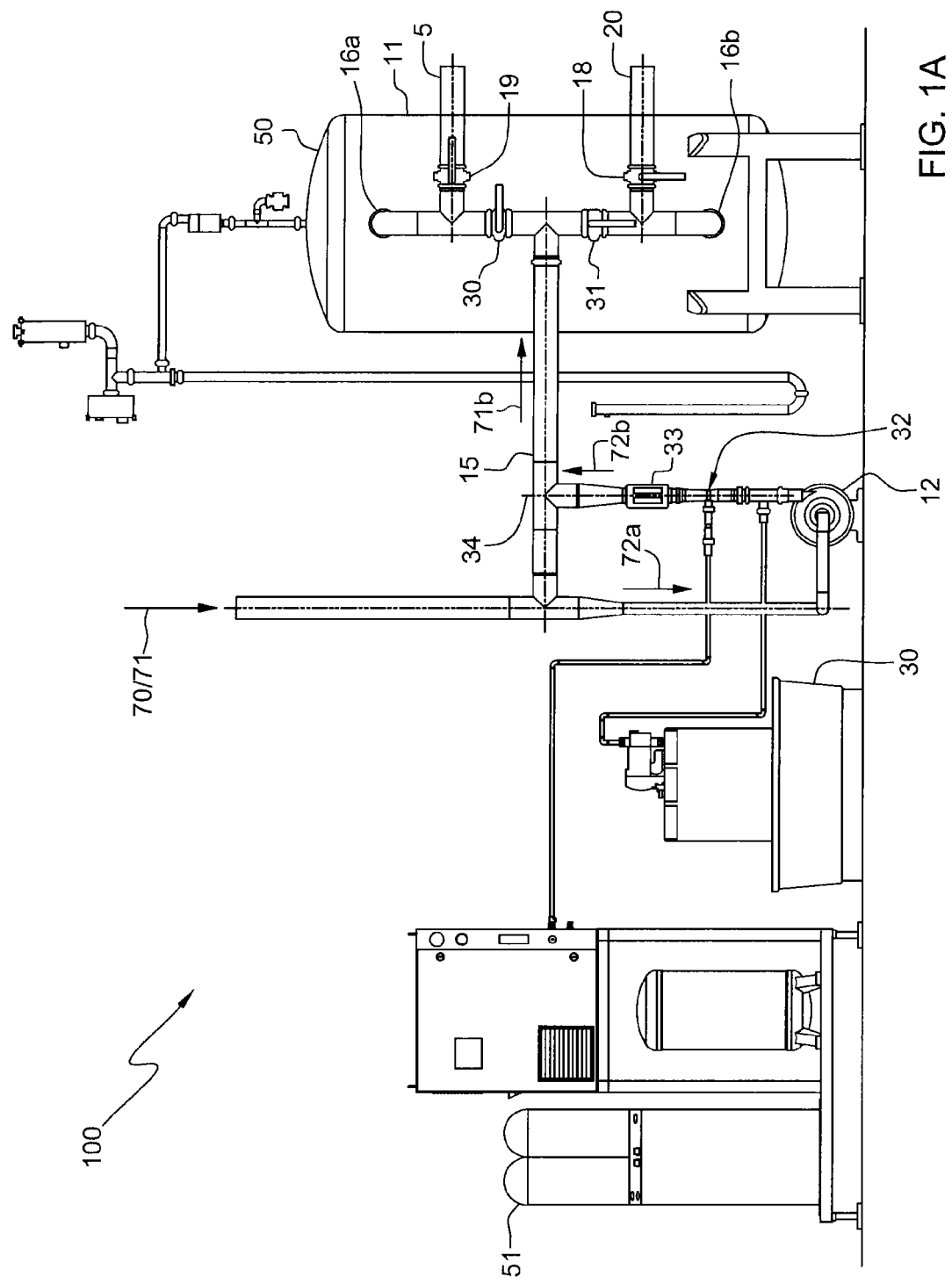
FIG. 1A shows one embodiment of a system configuration employing one embodiment of the method described herein.

Aspects of the present invention and certain features, advantages, and details thereof, are explained more fully below with reference to non-limiting embodiments. Descriptions of well-known materials, fabrication tools, processing techniques, etc., are omitted so as to not unnecessarily obscure the invention in detail. It should be understood, however, that the detailed description and the specific examples, while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure.

Definitions

The term "backwash" or "backwashing" refers to the process of flowing a backwash water stream counter-current to the treated water stream, thus reversing the flow of water back through a filter bed to remove contaminants or other non-adsorbed particles. "Backwashing" may also be referred to as "backflushing."

The term "activated carbon" refers to adsorbtive carbon particles or granules having a large surface area and a high internal porosity, usually obtained by heating a variety of carbon sources. "Activated carbon" may also be referred to as "active carbon" or "activated charcoal."

The term "granular activated carbon" (also known as GAC or "granulated" activated carbon) refers to activated carbon with a particle size ranging from about 0.2 to 5 mm.

The term "exhausted activated carbon" refers to activated carbon that has been depleted in its adsorption capacity. "Exhausted activated carbon" may also be referred to as "spent" or "depleted" activated carbon.

The term "ozone," or trioxygen, refers to the triatomic form of oxygen, an inorganic molecule with the chemical formula $OO_2$ or $O_3$ or O3.

The term "ozonated" describes a medium, compound, substance or liquid (e.g. water) that has been infused or impregnated with ozone. "Ozonated" may also be referred to as "ozonized."

The term "ozonation" refers to the treatment or combination of a substance or compound with ozone.

The term "ozone residual" or "residual" or "$C_{res}$" refers to the amount of ozone remaining in an aqueous solution after a certain contact time. "Ozone residual" may also be referred to as "residual concentration." When measured over time, it can also be measured as a CT value (see below definition).

The term "transferred ozone" or "$C_{init}$" refers to the amount of dissolved ozone per volume of water initially transferred to a water stream prior to dilution or depletion after a certain contact time. In accordance with this application, the transferred ozone can be measured as an aqueous concentration of milligrams per liter water (mg/L). For purposes of the application, this unit is the equivalent of parts per million (ppm).

The term "CT", for purposes of this application, refers to the residual ozone concentration ($C_{res}$) in mg/L multiplied by the backwash run time (T) in minutes (i.e. $C_{res} \times T$) for each cycle.

The term "ozone dose" refers to the amount of ozone added to the filter bed (wt/wt) during the course of a backwash run or cycle. In accordance with this application, the ozone dose can be measured as mg $O_3$/kg porous filter media.

The term "regeneration" refers to the removal of molecules adsorbed onto the surface of an adsorbent filter media to partially, substantially or completely restore said media to its original adsorptive capacity.

The term "reduced adsorptive capacity" refers to an adsorptive capacity less than a porous filter media's original, or native, adsorptive capacity.

The term "fluidization" refers to a process in which a feed water stream is passed through filter media at a sufficient flow velocity and with sufficient force to convert the granules or particles within the filter media from a static solid-like state to a dynamic fluid-like state such that the particles are suspended in the fluid flow and become agitated and/or reorganized.

The term "sanitization" or "sanitize" refers to the process of reducing the number of organisms or pathogens that endanger public health so as to reduce the microbial population to a safe level as determined by public health standards.

The terms "first upstream side" of the filter and the terms "first downstream side" of the filter, relate to the direction of the flow of water to be treated through the filter during the normal filtration or filtering step, mode or cycle.

The terms "second upstream side" of the filter and the terms "second downstream side" of the filter, relate to the direction of the flow of water during the backwash or cleaning step, mode or cycle.

The term "skid" refers to a piece of equipment that is modular and mounted on skids (skid-mounted) for ease of installation.

Detailed Description of the Embodiments

In one aspect, the invention provides a one-stage process that allows for the simultaneous sanitization and regeneration of porous filter media (e.g., granulated activated carbon or GAC) during a regular backwash cycle by mixing dissolved ozone with the backwash water. During the backwash cycle the GAC filter bed is expanded and fluidized so that each granule repeatedly contacts the dissolved ozone when the particles movement brings it to the bottom of the bed where there is sufficient ozone dissolved in the backwash water to both kill the bacteria and oxidize and desorb (or remove portions of) the contaminants. In this way, a fixed bed during filtration is converted to a fluidized bed during backwash.

FIG. 1A schematically illustrates filtration system 100 utilizing a downward flow, fixed (a/k/a "packed") bed pressure filter 50 together with a typical system configuration used in combination therewith. The components of system 100 shown in FIG. 1A, both upstream and downstream of filter 50, are largely conventional and will be described in a general, summary fashion with references to FIGS. 1A-1B and FIG. 2.

Figure 1B:
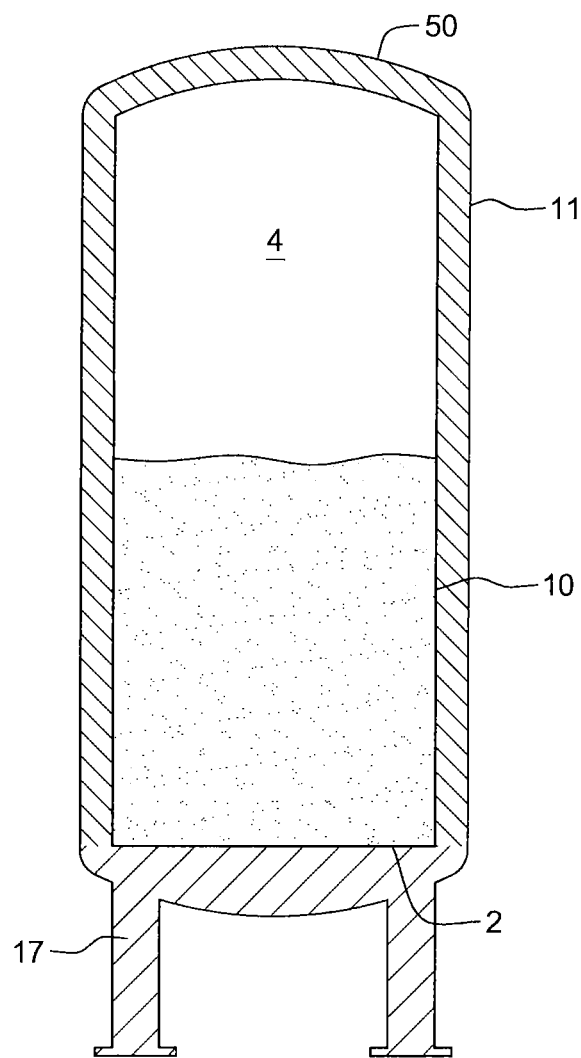
FIG. 1B illustrates the cross-section of the filter shown in FIG. 1A.

Referring to FIGS. 1A-1B, fixed bed-filter 50 comprises basin or vessel 11. As shown in FIG. 1B, fixed bed-filter 50 comprises GAC packed filter bed 10 within vessel 11. Filter bed 10 is supported by a filter bottom 2 (or inactive fill material). Often a system of interconnected nozzles is used to collect the filtered water during normal operation, and distribute the backwash flow during backwash. In embodiments of the invention, vessel 11 (or at least the under-drain system) is constructed of a material well known in the art to be resistant to dissolved ozone (e.g. stainless metal, [nickel-plated steel, alloy, ceramic, concrete, plastic]). One of ordinary skill in the art will recognize that for pressure filter systems shown in FIGS. 1A-1B, vessel 11 can be any type of tube, vessel, or cylinder suitable for filling or packing with filter media. In other embodiments where the inventive method is applied with different filtration systems other than pressure filter systems shown in FIGS. 1-2 (e.g. open gravity filters), vessel 11 may be, for example, rectangular or some other suitable configuration.

In embodiments of the invention, the process is not limited to filter systems that use activated carbon with a specific size (mesh), particular nature or morphology. In examples disclosed herein, lignite granular activated carbon (GAC) was used. However, the method described herein can be applied to any type of activated carbon, or other high porosity medium, that is employed and formed into filter bed 10 for the adsorption of contaminants (i.e. chlorine, organics) from a water stream. By way of example, in some embodiments, the process is employed with filter bed 10 comprised of GAC from bituminous coal, coconut, cherry, wood chips or wood char. The process can also be employed with GAC of various sizes, e.g. 8×30 mesh, 12×40 mesh, 4×10 mesh, etc. In still other embodiments, the process is used with GAC that has an effective size of 0.4 mm to 0.65 (coal base) or 0.8 to 0.9 (lignite base). The process also can be applied in filter beds that use carbon materials other than granular activated carbon, such as pelletized activated carbon. In still other embodiments, non-carbon based porous materials can also be used.

In the embodiment of the invention shown in FIG. 1A, filter vessel 11 is a pressure filter. While shown in a vertical configuration in FIG. 1A, vessel 11 may be configured vertically or horizontally within system 100. Vessel 11 can be any practical size, i.e. ranging in diameter from about ½ to about 10 feet, and the volume of porous filter medium comprising filter bed 10 in vessel 11 may have a range of about 1 cubic foot to about 500 cubic feet, including all ranges and subranges therein, limited only by practical considerations in the mechanical construction of the vessel. In embodiments discussed herein, vessel 11 has a length (or straight height) of about 2.25 m. In alternate embodiments, vessel 11 has a length (or straight height) in the range of about 0.5 m to about 5 m, including all ranges and subranges therein.

In other embodiments employing the method disclosed herein, vessel 11 is a gravity filter (not shown). For example, municipal water treatment plants often use open gravity type beds. Gravity filters operate on a similar principle as the filtration system shown here and, therefore, benefit similarly from the present invention. In some embodiments, although not meant to be limiting, they are open, and square or rectangular, with side dimensions in the range of about 2 to about 30 m, and media depth in the range of about 0.5 m to about 5 m, including all ranges and subranges therein. They are built from concrete, which resists dissolved ozone.

In accordance with the invention, vessel 11 (whether a gravity filter, pressure filter, or other type of filter) must have sufficient height to accommodate at least a 35% freeboard, excess capacity beyond the static filter bed designed capacity, to allow for bed expansion of filter bed 10 during backwashing.

In some embodiments, the weight of the filter media that forms filter bed 10 can be in the range of about 3 to about 5000 kg, including all values, ranges and subranges therein (3 kg, 10 kg, 100 kg, 1000 kg, 1950 kg, 2000 kg, 5000 kg, etc).

In the full scale test described herein (see below), the ozonation system of the invention is inserted or retrofitted into filtration system 100 operating at a filtration flow rate of about 2 to about 3 gallons per minute per square foot (gpm/ft$^2$) through 60 inches of activated carbon with an effective size of 2-3 mm. In other embodiments, the filter bed has a surface loading rate of about 0.015 gpm/ft$^2$ to about 8 gpm/ft$^2$ (i.e. 0.04-20 m/h) (for example, 0.015, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0 m/ft$^2$), including all values, ranges and subranges therein.

As described above, the inventive method can be employed with water treatment systems that employ different hydraulic loading rates (flow rates), various filter configurations (e.g. pressure or gravity), various filter depths and various types of filter media and still remain within the scope of this invention. Furthermore, methods of the invention can be retrofitted to water treatment systems that use a fixed bed of activated carbon media alone and/or the process can be used with a carbon adsorber system that immediately follows filtration by another media or filtration technique (e.g. sand, dual-media system) and still remain in the scope of this invention. Methods of the invention may be used with open gravity filters and mobile and fixed pressure adsorbers. In accordance with the invention, filter 50 may be configured as a cross-flow, or radial-flow, down-flow, up-flow filter.

Referring to FIGS. 1A-1B, the feed water or influent to be treated (70) is supplied to filter bed 10 by means of an feed water line (or influent conduit) 15 which delivers influent to be treated through feed water inlet 16a into the water chamber 4 upstream of the fixed bed filter 10. In this embodiment, inlet 16a is located upstream of and above filter bed 10. During filtration mode, valves 30 and 18 are open and valves 31 and 19 are closed (shut). The water to be treated flows in a first, or primary, filtration flow direction, shown here to be a downward flow, through the filter bed 10, resulting in filtered (or "treated") water being collected in collecting chamber 17. The filtered or treated water is removed from the chamber 17 by means of an outlet 16b and then flows through a treated (or filtered) water line or overflow pipe (or conduit) 20 located on the downstream side of vessel 11 which can be closed by any suitable shut-off element, i.e. a valve 18. In embodiments of the invention, the water lines, pipes, conduits, valves and other components of the system exposed to ozonated water during the backwash cycle are constructed of materials well known in the art to be resistant to ozone gas and/or dissolved ozone (e.g. stainless steel, Teflon®, PVC, glass, etc). The above described process is typical of a normal, filtration service run or cycle.

In a typical filtration system, the inlet (e.g. 16a) is usually at the top of the filter, above the filter media; the outlet (e.g., 16b) is usually at the bottom of the filter, below the filter media. The "feed" is the water going into the filter, which is directed to the inlet during normal filtration, and the outlet during backwashing. For most filter arrangements, the feed flow goes to the inlet at the top of the filter, flows downward through the media, and exits the outlet at the bottom of the filter, toward the filtered water effluent; flow is reversed during the backwash cycle, so that water from the feed enters the outlet below the filter media, flows upward through the media, exits through the inlet and is directed to the drain.

Periodically, the filtration cycle is stopped in order to initiate a backwash cycle. The backwash-ozonation system described herein is the principal subject of this disclosure and will be described in more detail herein.

In embodiments of the invention, the backwash cycle or step, which is well known in the art, utilizes filtered or otherwise purified water that is substantially free of chlorine or other contaminants. Most, if not all, filtration systems and equipment are provided with mechanical devices and control means for conventional backwash cycles wherein purified water flows in a direction substantially different from to the flow direction of filtration (i.e. the first, or primary, flow direction) in order to backwash or flush fixed bed 10 of loose particles. In accordance with the invention, the backwash flow direction (i.e. the "second flow direction") is different than, or substantially different than, the first flow direction used for filtration (i.e. by way of example only, countercurrent, opposite or normal). Second flow direction can comprise a flow upwards (see FIG. 1A & FIG. 2), downwards (not shown), or radially (not shown).

For example, although not meant to be limiting, in the embodiment shown in FIG. 1A at the upper portion of vessel 11 (i.e. upstream location during filtration mode), there is provided a backwash water line or drain pipe (or conduit) 5 or other equivalent structure which can be closed by any suitable shut-off element i.e. a valve 19. As shown in FIG. 1A, during the backwash cycle, valves 30 and 18 are shut (or closed off) and valves 31 and 19 are opened. This allows a purified backwash feed water stream 71 to flow via feed water line 15 through outlet 16b, thereby entering vessel 11 downstream of filter bed 10. The purified feed water stream then flows in a second flow direction (i.e. a flow opposite to the first flow direction of the feed water to be treated) through filter bed 10.

Figure 2:
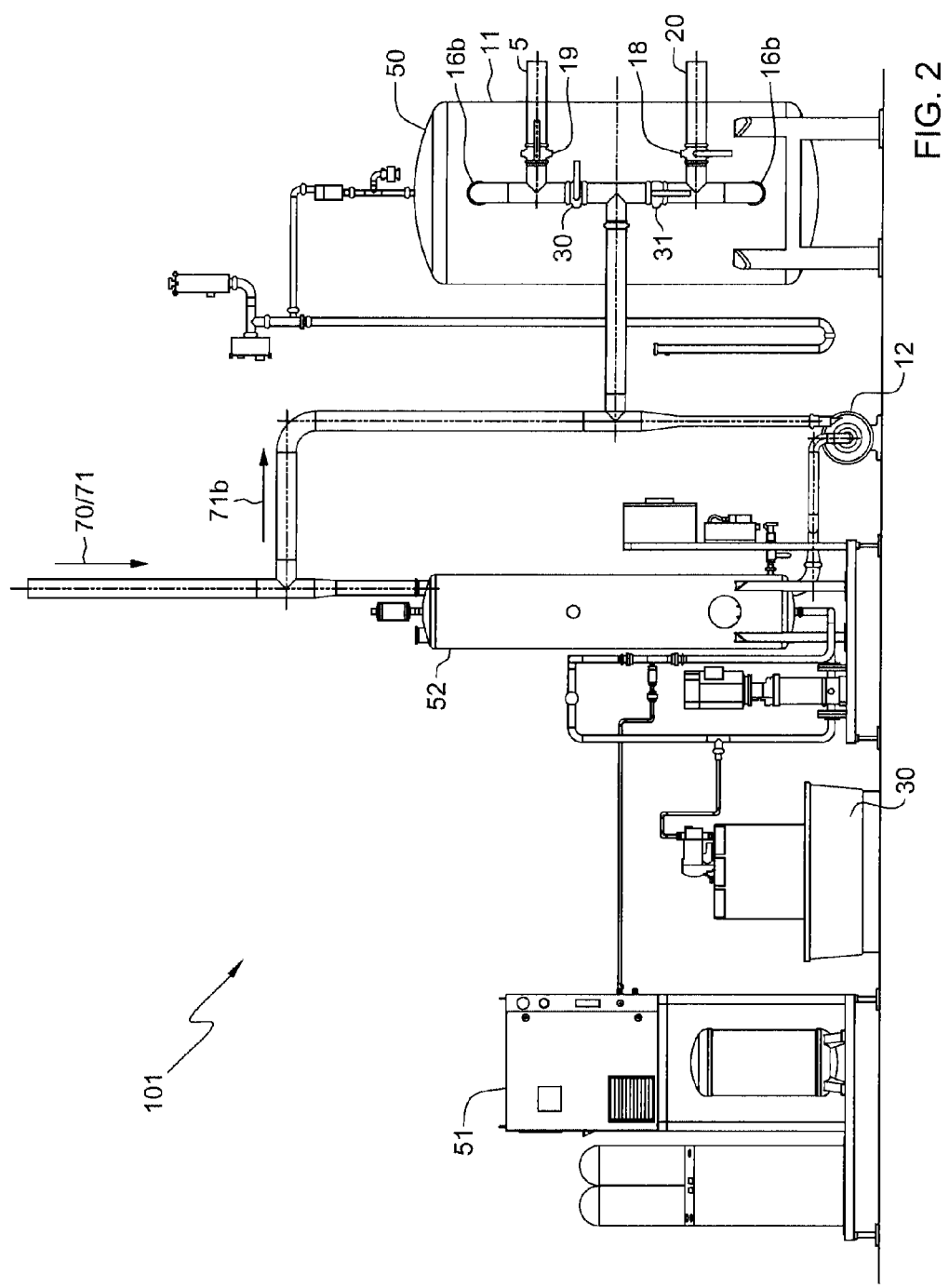
FIG. 2 shows one embodiment of a system configuration employing another embodiment of the method described herein.

Although the inventive method is described above with non-limiting references to the pressure filter shown in FIG. 1A-2, one of ordinary skill in the art will recognize that the operative backflow devices and configurations utilized in implementing the method will vary depending on the configuration of system 100. For example, during the backwash cycle of a gravity filter, there is no backwash shut off valve at the connection to the valve, only an overflow channel or canal (not shown). These alternate embodiments incorporating various configurations are still within the scope of the invention herein.

Second flow direction is different than first flow direction used during a normal filtration run. For example, second flow direction can be normal to or countercurrent to the first flow direction. In preferred embodiments, the second flow direction is an upward flow. The rapid upward flow washes away contaminants and bacteria, redistributes and resettles the filter medium bed, thus preparing it for another filtering cycle. In a configuration like that shown in FIG. 1a, drain pipe 5 allows the backwash water to be removed and collected in an overflow vessel or containment system (not shown), and then subsequently treated or otherwise disposed of or used. In a typical filtration system, although not meant to be limiting, the backwash cycle will continue until the turbidity of the backwash water is below an established value or the head loss across the filter has returned to an acceptable value, or the bacteria load of the filter bed is reduced to an acceptable level. In practicing the inventive method, one can use RLU or other similar biological measurements in the backwash effluent to determine when to stop the backwash step. Although an upflow backwash cycle is shown here in FIG. 1A, in alternate embodiments (not shown) the backwash feed stream is passed through filter bed 10 in down-flow or up-flow mode, depending on the filtration equipment that is being used and/or is already in place.

Referring again to FIG. 1A, during the backwash cycle of the inventive method, ozone is generated using ozone generation skid 51. By way of example, ozone generation Skid 51 can be a small-scale, compact ozone generator provided by a number of sources. For example, in certain embodiments, a compact Ozonia® OZAT® CFS-2G model generator is used. More specifically, a CFS-3 Model fed with 93% oxygen from an AirSep AS-D oxygen concentrator is used. In alternate embodiments, a different CFS-2G model can be used or a model from a different manufacturer.

One of ordinary skill in the art will recognize that modifying the type of ozone generator utilized or method for producing ozone (e.g. UV, corona discharge, cold plasm) will not impact the disclosure herein so long as said ozone generator has a production rate that provides the requisite dosage of ozone needed for the filter bed to be treated. For example, in accordance with embodiments of the invention, generator 51 should be capable of generating gaseous ozone within the range of about 100 g/hour to about 10,000 g/hour. Similarly, the source used to produce ozone (air or oxygen or water) will not affect the disclosure herein and is therefore not limiting. In a preferred embodiment, however, ozone generator skid 51 is compact, simple and flexible for easy integration (or retrofitting) into the current water treatment system, while at the same time has sufficient production capacity to ensure continuous operation at full-load in small to medium-size water treatment facilities.

In some embodiments, the method comprises means known to those skilled in the art for turning on ozone generator 51 when starting the ozonated-backwash cycle and then turning ozone generator 51 off once the ozonated-backwash cycle is finished. More specifically, the control system for ozone generator 51 will ensure flexible operation and allow integration into an established water treatment system 100.

In embodiments of the invention, ozone is generated at high concentration (6% to 20% by weight in oxygen ($O_2$)), including any and all values, ranges and subranges therein and dissolved in side stream 72, which comprises at least a portion of water stream 71, to create a continuous supply of ozonated water through outlet 16b. For example, in some embodiments, ozone is generated at a concentration of 6, 7, 8, 9, 10, 11, 12, 13, 14, 15, 16, 17, 18, 19, or 20% by weight (in oxygen). In alternate embodiments, but still keeping within the scope of the disclosure herein, ozone can be generated by any number of known processes in the art. For example, ozone generation system 51 can utilize air, instead of oxygen, to generate ozone. In this case, ozone will be generated at lower concentrations (i.e. 1-5% by weight in air (e.g., 1, 2, 3, 4, or 5 wt %)). On the other hand, if electrolytic generation of ozone is utilized, the concentration can be up to 30%, for example 6-30% (e.g., 6, 7, 8, 9, 10, 11, 12, 13, 14, 15, 16, 17, 18, 19, 20, 21, 22, 23, 24, 25, 26, 27, 28, 29, or 30 wt %), including any and all subranges and ranges in between (e.g., 6-25%, 10-20%, 15-30%, 20-30%).

In practice and in some embodiments, the inventive method comprises generating the ozonated-backwash solution as follows. Referring to FIG. 1A, a portion of the backwash feed water 71 is diverted via a side stream 72, injected with gaseous ozone at injection point 32, and then the resulting ozonated side stream is remixed with the main purified feed water at point 34. More specifically, a portion of the backwash water 71 is drawn from the feed water line via booster pump 12 incorporated into operative association with system 100 to produce a side stream 72. The side stream 72a then flows through injector 32 to aspirate the gaseous ozone into side stream 72b having an initial concentration of dissolved ozone in the water ($C_{init}$). In the embodiment shown here, injector 32 is a venturi injector. Side stream 72b having an initial concentration of dissolved ozone in the water ($C_{init}$) is then remixed with the remaining portion of backwash feed stream 71, producing a backwash feed stream $71_{comb}$ with a residual dissolved ozone concentration ($C_{res}$). Backwash feed stream $71_{comb}$, now with a residual dissolved ozone concentration ($C_{res}$), is introduced into filter bed 10 by means of feed water line 15 which delivers backwash stream $71_{comb}$ through outlet 16b downstream of the fixed bed filter 10. In the embodiment shown in FIG. 1A, outlet 16b is located at the bottom (downstream) of vessel 11 and filter bed 10.

In other embodiments, ozone concentration measurement devices are incorporated into operative association with system 100 to measure the ozone residual concentration and insure proper dosage control is maintained after ozone injection into the feed water and prior to introduction into the filter, and then to insure residual ozone is eliminated from the backwash stream exiting the filter, which eliminates the need for downstream removal of ozone.

In embodiments of the invention (see FIG. 1A), in particular embodiments wherein the filtration system is being used for disinfection, the pH of the backwash side stream 72a is monitored controlled, and/or adjusted to achieve a pH range of about 5.0-7.0 (e.g., 5.0, 5.5, 6.0, 6.5, or 7.0) prior to entering filter bed 10. To achieve this pH range, pH adjustment system 30 (or pH control) is included in system 100. For example, in certain embodiments, the desired pH is achieved via pH adjustment system 30 by injecting acidic chemicals upstream of venturi injector 32. In other embodiments, the desired pH is achieved via pH adjustment system 30 by injecting basic chemicals. In certain embodiments, this pH adjustment step also services as a mixer. One of ordinary skill in the art will recognize that any suitable system for monitoring and adjusting the pH of the feed water can be incorporated.

One of ordinary skill in the art will also recognize that while the above pH range is suitable for disinfection, a different pH range may be required for other filtration applications. For example, one of ordinary skill in the art will also recognize, that in alternate embodiments, the inventive method can be used to adsorb non-organics, such as chlorine. And in still other embodiments, the method can be employed to oxidize hazardous contaminants, such as arsenic or phenols, filtered from a waste stream. In the latter case, one of ordinary skill in the art will recognize that an increased pH in the range of about 8 to about 10 (e.g., 8.0, 8.5, 9.0, 9.5, or 10.0) would be preferred to enhance the oxidizing potential of ozone by generating OH° free radicals.

In certain embodiments, as shown in FIG. 2, ozonation-backwash system (101) includes ozone mass transfer skid 52. Ozone mass transfer skid 52 allows for the dissolution of ozone into the feed water at high pressure (e.g., 50 to 500 psi, (e.g., 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 psi)) including any and all ranges and subranges therein). For example, in some embodiments, ozone is dissolved in a water stream at a pressure of 50, 75, 100, 125, 150, 175, 200, 225, 250, 275, 300, 325, 350, 375, 400, 425, 450, 475, or 500 psi. To improve ozone transfer efficiency from ozone generator 50 and improve the mixing of ozone with the backwash water side stream, the gaseous ozone can be injected into a recirculation loop so that water flow through static mixing element, or contact chamber, 52 is countercurrent to the ozonated water stream from injector.

Whether via venturi 32, mass transfer skid 51, a static mixer, bubble diffuser, or some other means of mixing and dissolving ozone into the feed water, the resultant ozonated water 72b is mixed with backwash feed water 71 to produce backwash feed stream $71_{comb}$, with a residual dissolved ozone concentration ($C_{res}$). Backwash feed stream $71_{comb}$ then enters the bottom of filter bed 10 through water line or conduit 15 via outlet 16b, which can be closed by any suitable shut-off element, i.e. a valve 18, once the backwash cycle is completed. Next, the backwash process cycle is initiated and run using backwash feed stream $71_{comb}$ and with direction of flow ("second direction of flow") that is substantially different from the direction of flow during the normal filtration cycle (i.e. the "first direction of flow"). For example, second flow direction may be normal to, opposite to, or counter-current to first flow direction. Upon completion of the backwash cycle, system 100/101 is returned to normal filter operation, without the need to let filter bed 10 rest or to further flush or rinse filter bed 10.

In accordance with embodiments of the invention, the water flow velocity employed during the backwash cycle is sufficient to achieve substantial, or preferably complete, fluidization of filter bed 10. For purposes of this application, this is referred to as a minimum fluidization velocity. In preferred embodiments of the invention, the minimum fluidization velocity is between about 20-50 m/h (8-20 gpm/ft$^2$) (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 m/h), including any and all ranges and subranges therein, with a preferred velocity of about 25 m/h. In certain embodiments, depending on the size of the porous particles and other factors such as volume of the tank, etc, the minimum fluidization velocity will vary from about 5 m/h to about 60 m/h (2-24 gpm/ft$^2$) (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 m/h), including any and all ranges and subranges therein. For example, in some embodiments, a predetermined, target minimum fluidization velocity will be about 5, 6, 10, 12, 15, 20, 23, 25, 26, 30, 35, 40, 45, 50, 55, 60 m/h, while in practice it will vary and for a single cycle, may fall within a given range or subrange (e.g. 5-20 m/h, 5-15 m/h, 15-30 m/h, 20-35 m/h, 26-40 m/h, 25-55 m/h, 40-50, etc).

Achieving a predetermined minimum fluidization velocity for the backwash cycle will fluidize, expand and agitate the porous filter medium contained within filter bed 10. In reference to FIG. 1A, during this process, the bed will expand upward. For an optimal backwash regime it is important that all, or substantially all, of the carbon particles are fluidized. In certain embodiments, this requires the backwash flow to be adjusted to obtain a minimum bed expansion of at least about 35%, and a preferred expansion of 50%. In other alternate embodiments, complete fluidization can be achieved with a flow rate high enough to expand the filter bed by 20-35%. One of ordinary skill in the art will recognize that the minimum fluidization velocity required to fluidize a filter bed will vary from system to system, depending on various characteristics of the water treatment system and fixed bed filter incorporated therein. More specifically, it will be affected by and directly related to media type, particle size, uniformity coefficient, water temperature, and salinity. For example, a backwash velocity of 35 m/h may result in a bed expansion between 20 and 55% depending on the GAC type. By way of further example, depending on the filter bed characteristics, backwash flow velocities between 25 and 55 m/h may be required in order to achieve complete, or substantially complete, fluidization. One of ordinary skill in the art will recognize that a fluidization test should be used to identify the appropriate predetermined minimum fluidization velocity to achieve full, or substantially full, fluidization.

In certain embodiments, the backwash cycle takes about 10 minutes to 45 minutes, preferably about 10 minutes. In others, the process involves a backwash cycle that of between about 5 to about 60 minutes (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes), including any and all ranges and subranges therein (e.g., 10-20, 25-35, 30-40, 10-50, 20-55, 5-20, 40-50 minutes). Although the above ranges are typical, the length of time will be different from filter to filter and therefore must be experimentally determined. For example, in some embodiments, depending on various factors (e.g. the nature and quantity of the adsorbed organics and material to be removed, the length and composition of the filter bed, the requisite residency time, temperature, etc.), a backwash cycle may take more than 60 minutes (e.g. 1.5, 2.0, 2.5 hours, or more). A predetermined back wash cycle time can be optimized to obtain a desired level of sanitization, and also regeneration when appropriate, in accordance with the knowledge of those skilled in the art (e.g. for sanitization, this can include a measurement of RLU of a water sample drawn from the bed, or other similar biological marker). Although the backwash cycle time may vary depending on the system, the length of downtime for system 100/101 will be substantially equivalent to the predetermined backwash cycle time, as in most cases an additional rinsing step will not be needed and the system can return to normal operating mode immediately following the backwash cycle. In accordance with this application, sanitizing does not require complete elimination or destruction of all bacteria, but only near (or substantial) elimination. By way of example only, in some embodiments, "sanitization" refers to a reduction in organism or pathogen count of at least 99% (e.g., at least 99.5% or at least 99.9%).

In some embodiments, in particular embodiments wherein organics are being filtered, the invention provides a pH of about 6.0 and residual ozone concentration of 1.6 mg/L for the backwash feed stream, which affords excellent sanitization in about 15 minutes. This corresponds to a CT of about 24 mg/L-min and an ozone dose of about 150 mg O3/kg porous filter media. At a pH of 6.5, an ozone dose of about 180 mg O3/kg porous filter media is required for sanitization. In some embodiments, the inventive method utilizes a CT of about 5 to about 50 mg/L-min, including any and all ranges and subranges therein). For example, in some embodiments, the method utilizes a CT of about 5, 6, 7, 8, 9, 10, 15, 20, 24, 25, 30, 40 or 45 mg/L-min. Generally, as higher ozone concentrations are used, required backwash time decreases.

The Environmental Protection Agency (EPA) uses CT (concentration×time) factors to determine disinfection of drinking water, and the same concept applies to ozone concentrations for the present invention. For purposes of the application, the CT value is measured at the point where the ozonated backwash is fed, or otherwise introduced, into the filter during the backwash cycle (i.e. at the filtration outlet on the "first downstream side" which is also the "second upstream side"). In addition, for purposes of this application, the term "ozone dose" is a design parameter for defining the inventive method herein. It will vary with the type and quantity of contaminants to be filtered. One of ordinary skill in the art will recognize however that, for a given filter with a preset backwash flow, CT is directly proportional to the ozone dose as defined herein and easier for operating personnel to quantify, thus being a more practical day-to-day operating parameter.

Activated carbon filters designed for sanitization are generally constructed of stainless steel which resists well the dissolved ozone. Additionally, as shown by the results herein, the fluidized activated carbon is not damaged by the dissolved ozone. Therefore, the maximum dissolved ozone level is limited only by practical considerations of equipment cost and ozone mass transfer. By way of example, in some embodiments, the effective or residual concentration of dissolved ozone ($C_{res}$) is 0.5 mg/L to 12 mg/L (e.g., 0.5, 1, 2, 3, 4, 5, 6, 7, 8, 9, 10, 11, or 12 mg/L), including any and all ranges and subranges there (e.g. 0.5-3.0 mg/L, 1-5 mg/L, 2-5 mg/L, 1-2 mg/L, 5-10 mg/L, 8-12 mg/L, etc.). One of ordinary skill in the art will recognized that higher residual ozone levels (e.g, 10 mg/L or greater) are associated with added expense (e.g. equipment cost) as compared to lower ozone levels.

In practice, the residual ozone concentration of the backwash feed stream can be measured by any known means in the art. For example in certain embodiments, residual ozone is measured by the indigo method using a Hach spectrophotometer. However, alternate embodiments may use the UV absorption method, membrane sensor methods, stripping and gas phase detection, and/or include remote or on-line monitoring and controls.

In certain embodiments, due to mass transfer inefficiencies and ozone demand in feed water 7I, there is a need to apply a higher dose of ozone ($C_{init}$) to achieve the target, residual dissolved ozone concentration ($C_{res}$) for backwashing. For example, for illustration purposes and in no way meant to be limiting, if the requisite level of residual dissolved ozone for backwashing ($C_{res}$) is 1.6 mg/L, then introducing an ozone dose ($C_{init}$) of about 2.5 mg/L ozone into feed water 71 may be required in order to achieve the target residual concentration ($C_{res}$). Similarly, in some embodiments, the method disclosed herein will use only a portion of the full backwash flow for the side stream ozone injection. By way of example, if only one-quarter (¼) of the full backwash flow is utilized for side stream ozone injection, one of ordinary skill in the art will recognize that the side stream ozone concentration will subsequently be diluted when it is mixed with the remaining ¾ of the backwash feed stream. Therefore, in the above example, an initial ozone dose (i.e. the transferred ozone or $C_{init}$) of about 10 mg/L ozone must be introduced into the side stream 72a diverted for ozone injection in order to ultimately achieve a target residual concentration for fluidization equal to about 1.6 mg/L ($C_{res}$) in feed stream 71$_{comb}$.

To keep the gas to liquid ratio in a range appropriate for efficient gas transfer, the method uses the relatively high concentration of ozone in gas discussed above (e.g. 6%-20% by weight in $O_2$).

The temperature at which the process is run may be any temperature at which the process works. Generally, the temperature limits for the method disclosed are between about 1° C. and about 30° C. (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C.), most preferably about 20° C. In some embodiments, the method can be operated at ambient conditions, including temperature. In others, those skilled in the art will recognize that the temperature may affect the process by introducing reduced ozone solubility and half-life (high temperatures), reduced reaction rates (low temperatures), as well as other difficulties with operating at high temperatures. In these situations, temperature may need to be monitored and controlled, if feasible.

Using the one-stage process disclosed herein, the residual dissolved ozone introduced into the system is quickly depleted during the backwash cycle. As such, in some embodiments, the inventive method requires the filter bed only to be down (or offline) for a length of time roughly equivalent to the length of the backwash cycle (e.g., 10-20 minutes) already in place within the treatment system. For example, in some embodiments of the inventive method, one can start to use filter 10 immediately following the backwash step because filter 10 contains only clean water with no remaining trace chemicals. This is compared to 8 to 24 hours, or more, of down time for conventional chemical sanitization, which requires prolonged rinsing to remove the chemicals, which wastes water, requires a longer down time for filter 10 and contaminates the environment. This feature also makes the invention described herein particularly suitable for retrofitting an existing treatment system without significant disruption or difficulty. While not required, in a variant of the preferred embodiments of the process, the invention disclosed herein comprises the optional step of washing with filtered or pure water following the ozonated backwash step. This optional washing step would be implemented using methods and parameters known in the art.

Activated carbon filters designed for sanitization are generally constructed of stainless steel which resists well the dissolved ozone. Large gravity filters are generally constructed of concrete which also resists well the dissolved ozone. This constitutes another feature that makes the invention described herein particularly suitable for retrofitting an existing treatment system without significant disruption or difficulty.

In still other embodiments, microbiological testing methods known to those skilled in the art are used during startup to determine the required residual concentration and backwash time (CT) for sanitization. When required, in some embodiments, provision is made for purging and destroying excess ozone, and insuring that operators are not exposed to unsafe levels in air.

During backwash the filter bed is expanded and fluidized, which allows granules to repeatedly contact the ozone when the particles movement brings them to the bottom of the bed where there is sufficient ozone dissolved in the backwash water to kill bacteria and oxidize contaminants. In the methods disclosed herein, any expansion parameters may be used as long as they allow the filter bed to be in movement so that all granules are progressively exposed to the high ozone residual at the bottom, thus affording effective sanitization and regeneration. In a non-limiting embodiment, a target expansion of 35-50% is used. Those of ordinary skill in the art will recognize that the appropriate backwashing model for each water treatment system will depend on a number of factors, including for example the different operating conditions and different grain size of the porous filter material, and that this in turn will affect the target range for the minimum fluidization velocity and bed expansion.

As discussed, in some embodiments, the inventive method does not require or comprise backwashing the filtration bed with non-ozonated water following the ozonated-backwash step (i.e. no rinsing of the filtration bed is required). This is because, in such embodiments, any dissolved ozone is consumed by the carbon itself, and therefore no rinsing is required prior to placing the fixed bed into operation (i.e. filtration mode). This is an advantage to conventional techniques in that it results in water/energy savings, decreased down time for the filter and additional cost savings.

As depicted in FIG. 2, other embodiments use an ozone generation skid 51 combined with a mass transfer skid 52 to produce ozonated water that can be injected into the feed water line upstream of the filter. While this involves more equipment, it has the advantage of producing ozonated water that can be used for Clean-in-Place (CIP) of other process equipment and pipelines in the same plant.

In yet another aspect of the invention, a system is provided capable of carrying out the inventive process of the first aspect of the invention. In some embodiments the inventive system may be retrofitted or operatively incorporated into an already existing system. The inventive system comprises operatively selecting and installing devices which are needed for the ozonated backwashing operation into existing plants or systems. The conversion of the water treatment plant to incorporate the system of the invention requires minimal down time and financial expenditure. By way of example, in some embodiments the conversion of the system comprises the following steps: two insertions are made into a water pipe that feeds a filter; one to supply water to the ozone injection device and another to remix the ozonated water with the backwash water. If the filter uses a different supply for backwash water than the regular feed water (for example a filtered water reservoir and pump for this purpose), these insertion points should be after the backwash water insertion point.

As described above, the inventive methods and systems are suitable for use in anywhere from small to large scale applications. In some embodiments, the inventive methods and systems are applied at small industrial scale water plants. In some embodiments, the inventive methods and systems are applied at large (e.g., municipal) water plants. In some embodiments, the invention methods and systems are applied to treat municipal wastewater, surface water, industrial process water or waste water, drinking water, and groundwater.

In some embodiments, the inventive methods and systems utilize ozonated backwash to control bacterial growth on activated carbon in minutes (e.g., 5-60 minutes), as compared to hours for conventional methods, and these periodic short sanitization cycles can regenerate and extend the useful life of the carbon.

In a further embodiment, the process includes the additional step of determining a predetermined minimal fluidization velocity for the filtration bed to be sanitized and/or regenerated. In yet another embodiment, the process includes the additional step of calculating the residual concentration of dissolved ozone ($C_{res}$) and backwash interval (T, =length of backwash cycle) required to achieve the requisite CT value to achieve sanitization.

In other embodiments, the process includes the additional step of calculating the requisite ozone dose (mg $O_3$/kg porous filter media) required to insure sanitization, which will usually be in the range of 10 to 300 mg/kg (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, or 300 mg/kg) over the course of a single backwash cycle, including all values, ranges and subranges in between (e.g. 10-15 mg $O_3$/kg, 10-100 mg $O_3$/kg, 30-100 mg $O_3$/kg, 10-200 mg $O_3$/kg, 50-200 mg $O_3$/kg, 150-300 mg $O_3$/kg, mg $O_3$/kg). Depending on the characteristics of filtration system 100, over the course of year, the cumulative ozone dose may be in the range of about 1 g $O_3$/kg porous filter media to about 30 g $O_3$/kg porous filter media (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 g $O_3$/kg porous filter media), including all values, ranges and subranges in between (e.g. 1-5 g $O_3$/kg, 1-10 g $O_3$/kg, 3-10 g $O_3$/kg, 1-20 g $O_3$/kg, 5-20 g $O_3$/kg, 15-30 g $O_3$/kg, 20-30 g $O_3$/kg). As discussed above, the calculated ozone dose required is directly proportional to the calculated CT value required.

Pilot Scale Demonstration

The invention will be further understood, but not limited, by the following pilot scale testing and results. More specifically, in these tests, we conducted pilot scale tests to: (1) quantify the amount of regeneration and sanitization by the novel process; and (2) calculate a target ozone dose (mg $O_3$/kg porous filter media) to insure sanitization during full scale tests.

A pilot scale (50 mm internal diameter×1000 mm tall) filter was built and loaded (to a depth of 400 mm). The adsorption capacity of the activated carbon was depleted as a consequence of its use to filter water from a pond with fish and turtles over several months prior to the tests.

A measure for evaluating the micropore volume (i.e. adsorptive capacity) of activated carbons can be established by measuring the Iodine Number (IN) according to ASTM D4607-94, "Standard Test Method for Determination of Iodine Number of Activated Carbon." A higher value for the IN corresponds to a higher micropore volume, which corresponds to a higher adsorptive capacity. Using method ASTM D4607-94, the degree of depletion was determined by comparing the measured iodine number (IN) of the fresh (or "virgin") carbon (950 mg/g) to the depleted carbon (630 mg/g).

Backwash flow was adjusted to obtain a bed expansion of 50% in all tests, which corresponded to an empty bed water flow velocity of 43 m/h. In the first run, clean water without ozone was used to backwash the depleted carbon, and samples were taken at intervals to determine the possible effect of regular backwashing on carbon regeneration. 40 minutes of backwashing without ozone increased the IN to 760, a recovery of 40% of the lost capacity by simple scrubbing. In subsequent runs ozonated water was used for backwashing.

Results

Figure 3:
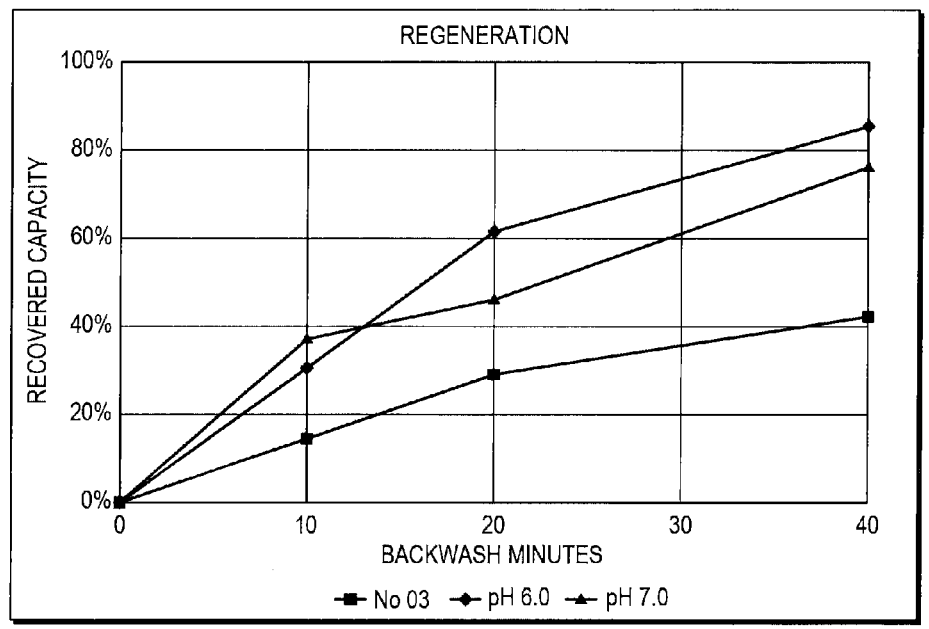
FIG. 3 is a chart showing regeneration pilot scale test results.

FIG. 3 is a chart showing regeneration testing results. The residual ozone concentration ($C_{res}$) in the backwash water feed was 1.6 mg/L. 40 minutes of backwashing with ozonated water increased the IN to 890, a recovery of 80% of the lost capacity. Tests at pH 6.0 and 7.0 showed little difference in adsorptive recovery.

Figure 4:
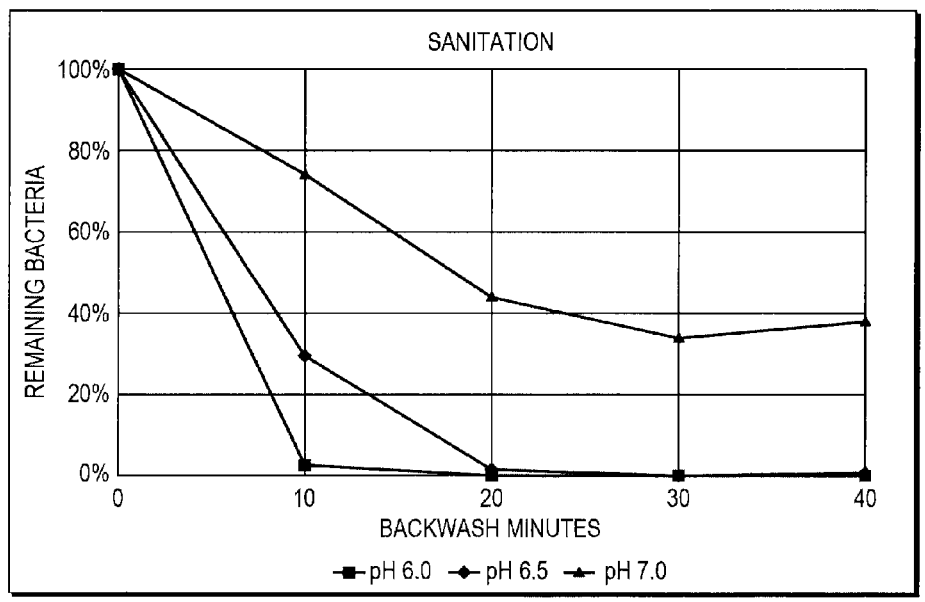
FIG. 4 is a chart showing sanitization pilot scale test results.
Figure 5:
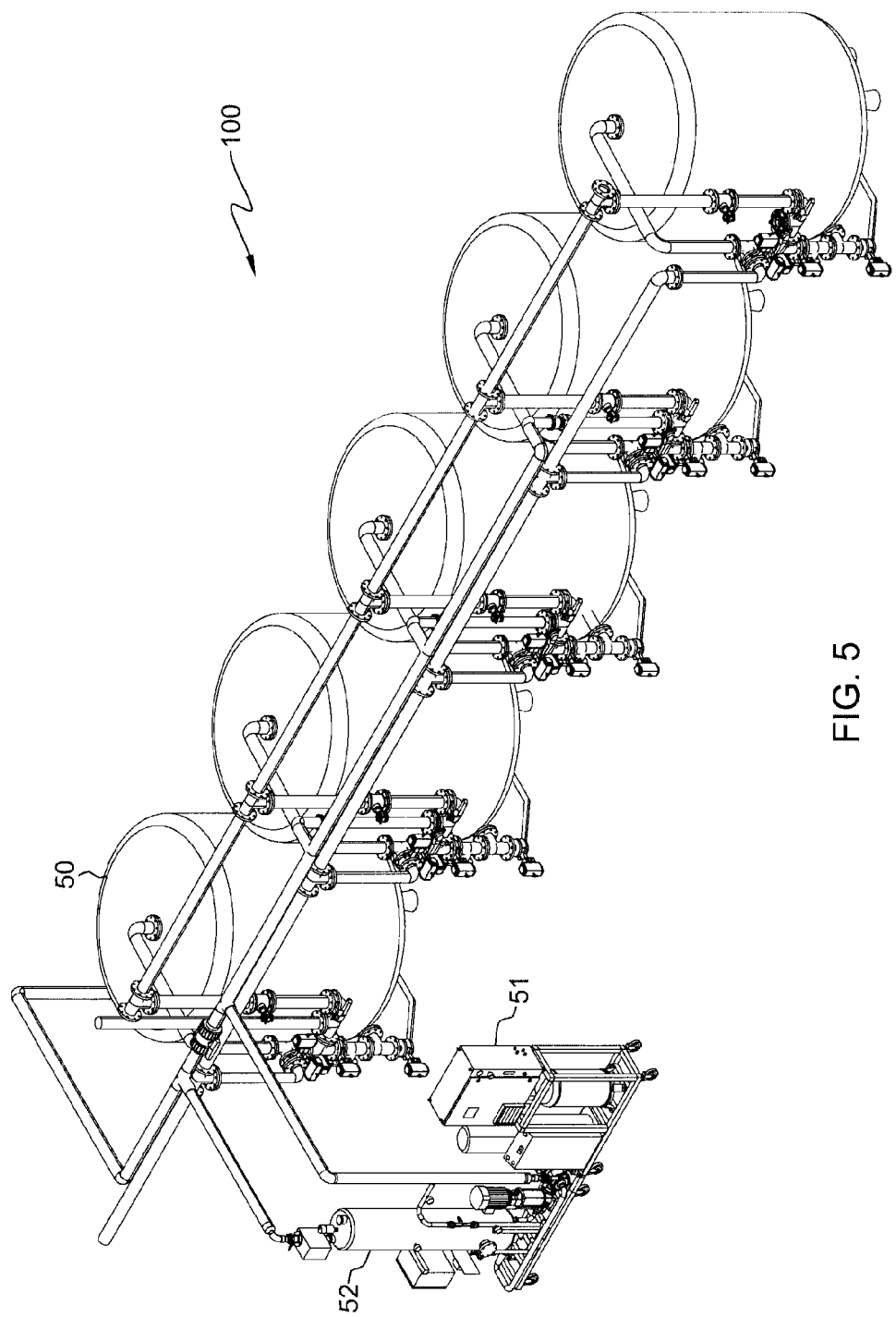
FIG. 5 illustrates one embodiment of a system configuration retrofitted into a water treatment system.

FIG. 4 is a chart showing sanitization testing results. Sanitization of the carbon was measured by testing for Total Bacterial Count in a sample of water drawn from the bottom of the filter bed, with backwash halted, after discarding 200 mL of sample so that it would be representative of conditions in the carbon bed. Tests at pH 7.0, 6.5 and 6.0 showed significant improvement by lowering pH from 7.0 to 6.0. Bacterial reductions after just 10 minutes of backwashing with ozonated water were 26%, 71% and 97% at pH 7.0, 6.5 and 6.0 respectively.

The resulting hardness of the activated carbon was tested by shaking 100 g carbon samples, dried after exposure to ozonated backwash, in a container with steel balls, using a mechanical shaker for a fixed time period, and then sieving and weighing fines. No significant loss of hardness was found, demonstrating that extended exposure of the activated carbon to the dissolved ozone did not lead to cracking or pulverization by abrasion during the backwashing step or result in subsequent loss of carbon to drain.

Visual observations, on a macro scale, were performed following treatment with ozonated backwash. A direct side-by-side comparison of ozone treated carbon samples with untreated carbon samples removed prior to treatment confirmed that the carbon granules were thoroughly cleaned by the ozonated backwash. Specifically, these observations indicated the treated carbon samples were darker in color and shinier as compared to the exhausted carbon samples. In contrast, carbon samples subjected to conventional backwash were lighter in color and opaque. The ozonated samples were the most similar in appearance (i.e. color and reflectance) to the virgin samples.

Visual observations, on a micro scale, also were performed following treatment with ozonated backwash using an optical microscope. These micro-scale observations indicated the surface of the ozone-treated carbon granules was restored to near-virgin conditions of cleanliness and porosity as compared to the exhausted carbon samples. In contrast, carbon samples subjected to conventional backwash had pores that were blocked and unavailable for contaminant adsorption. Again, the ozonated samples were the most similar in appearance to the virgin samples.

Discussion of Results

The small scale pilot testing indicates 20 minutes of backwashing was sufficient to sanitize the carbon bed at a pH of 6.5 (see FIG. 4), which corresponds to an ozone dose of 180 mg $O_3$/kg C to achieve sanitization. This is a surprisingly insignificant amount of ozone as compared to other chemical treatment methods.

Conventional sanitization or bacterial control for activated carbon filters is usually done by backwashing, followed by steam or chemical treatment. Steam treatment requires significant energy expenditure, and time to empty, heat up, hold the temperature, cool down and refill the filter, as well as risk to operators from high surface temperatures, and loss of carbon to heat damage. The full steaming cycle takes about 24 hours. In practice, cooling the carbon after steam sanitization tends to fracture the carbon granules producing fines. This causes carbon loss and requires expensive polishing filters positioned immediately after the carbon filters, wherein the polishing filters need to be replaced every few weeks.

Chemical treatment involves raising the pH with caustic soda, soaking for at least 4 and up to 24 hours, and then prolonged rinsing which wastes water.

The pilot studies show that bacterial control with ozonated backwash can be achieved during the regular backwash cycle in as little as 10-20 minutes, which can be increased if necessary to achieve the desired level of sanitization. 10 minutes is a fairly typical backwash time for a GAC pressure filter.

Full Scale Test

A full scale test was conducted on a filter of 2.10 m diameter and 2.25 m straight height, loaded with 2000 kg of Clarimex CAGR (8×30 mesh) lignite granular activated carbon, available from Clarimex, S.A. de C.V. (Mexico). The IN for the virgin carbon is 600. In practice, the filters used for the full scale test were used for dechlorination.

The filter had been in operation for 8 days since the previous steam sanitization. Two test runs were performed on the same filter, with normal filtration operation between runs (no downtime, rinsing or backwashing).

Filtered water was used for backwashing, to insure that no chlorine would be present, and a fraction of the backwash water was diverted through the ozone injection equipment then remixed with the main flow. Ozone was produced using an Ozonia CFS-3 generator, producing 143 g/h of ozone under the test conditions. The ozonator was fed with 93% oxygen from an AirSep AS-D oxygen concentrator.

The ozone was injected using a venturi injector in a recirculation loop so that water flow through the contact tank was counter to ozonated water stream from the injector, to improve ozone transfer efficiency. Some ozone was lost to offgas and reversion to oxygen, so that actual residual concentration ($C_{res}$) of dissolved ozone in the backwash inlet (or feed) stream to the carbon filter was 0.8 mg/L and the applied ozone was 114 g/h. The residual ozone was measured by the indigo method using a Hach spectrophotometer.

During preliminary hydraulic testing at the plant, it was found that the maximum flow obtainable with all four (4) production lines in operation was 1500 L/m. Based on the characteristics of the Clarimex CAGR activated carbon, it was determined flow rate would achieve a sufficient minimum fluidization velocity for 35% bed expansion and full fluidization.

During the first run (Test 1), one of the production lines was out of service during the backwash cycle. This increased the backwash flow to about 2350 L/m, which corresponded to a 60% bed expansion. Over the course of the test, the flow ranged from 2020 L/m to 2354 L/m.

The pH of the filtered water used as the backwash feed stream was 6.5. No adjustment for pH was made. Using the pilot scale results as a guide, it was determined that as a pH of 6.5, a target dose of ozone would be equivalent to 180 mg $O_3$/kg C in order to achieve acceptable sanitization levels. Using this as a guide, it was determined a backwash cycle of 2.5 hours should be used to provide a minimum dose of 160 mg $O_3$/kg C.

A sample of the activated carbon was drawn from the filter before and after the test to determine the adsorptive capacity. Water samples were drawn before and after the test, and after each 25 minutes of backwashing, including an extra sampling at 12.5 minutes, by the following procedure: Backwashing was paused for 5 minutes to allow dissolution of bacteria from the carbon into the water. Then the backwash was run without ozone at a flow rate of 1100 L/m (the flow obtained with the ozone side stream shut down). After 30 seconds samples were drawn from the effluent stream for later determination of heterotrophic plate count, bromate and trihalomethane.

During the second run (Test 2), the flow rate was adjusted to the target minimum fluidization velocity (i.e. to achieve full fluidization), about 1500 L/m (actual range was from about 1425 to 1670 L/m). The backwash cycle was run for 1.5 hours. Samples for RLU and HPC were drawn from the effluent during intentional pauses in backwash for this purpose, after a 5 minute pause followed by backflow at a non-fluidizing flow rate. Carbon samples were extracted from the bed before and after each run, to determine iodine index.

On-the-spot measurement of RLU (Relative Light Units) for both Test 1 and Test 2 were completed using a Kikkoman Lumitester model PD-20 as an approximation of the remaining bacterial load in the water samples, as well as the carbon samples. RLU measurement, a marker for bacterial presence, measures the presence of adenine triphosphate or ATP in the sample, which in turn is indicative of the number of viable cells present in a sample RLU measurement of ATP has been described in a number of references including U.S. Pat. Nos. 3,745,090, 3,941,703, 3,933,592, and 4,246,340 as a rapid and sensitive method for determining the number of viable bacterial cells in a sample. The RLU vs. the cumulative ozone dose for Test 1 (RLU1) and Test 2 (RLU2) are plotted and shown in FIG. 6.

Results

Figure 6:
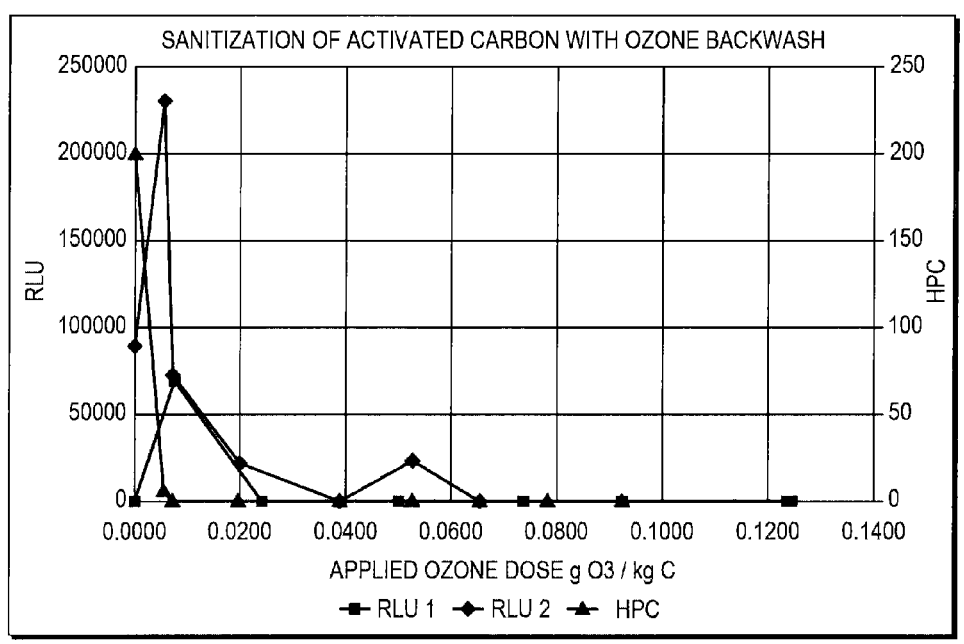
FIG. 6 is a chart showing the sanitization results (RLU vs. ozone dose) from a full scale test results.

As can be seen in Table 1 below and in FIG. 6, initial RLU readings for Test 1 were 481 in water samples. The RLU number for the carbon samples was 7. All subsequent measurements, from 12.5 minutes onward of ozone backwash, gave readings of 0 RLU. The high initial peak and rapid decline of RLU in the backwash indicates relatively efficient backwash. Similarly, while initial RLU readings for Test 2 were much higher (88826) in the water samples, RLU readings after a 10 mg $O_3$/kg C hit 0 after 1.25 hours of backwash. Initial heterotrophic plate count greater than 200. After 1.25 h ozone backwash 0, after 2.5 h, 1.

Table 2 measures the iodine index (a measure of adsorptive capacity of the carbon) against the cumulative ozone dose of both Test 1 and Test 2.

A 10 mg $O_3$/kg C dose per backwash cycle is sufficient to sanitize (or nearly eliminate bacteria from) the activated carbon in this fairly typical industrial application. For this particular system, this dose can be achieved in only 45 minutes. A target dose of 180 mg $O_3$/kg C might be appropriate for heavily contaminated carbon.

In both tests, the Iodine index increased, indicating regeneration of the activated carbon. Although the % regeneration was not as significant as that seen in the pilot scale test which treated GAC with significant organic exhaustion, in sanitization applications such as those similar to the full scale test herein, regeneration will occur gradually in response to the accumulated dose over several backwash cycles.

For both tests, the water consumption used was similar to that used for steam sanitization and much less than used for caustic sanitization. Shorter backwash cycle times, and less water consumption, could be obtained with a higher ozone production capacity.

TABLE 1

RLU and HPC results for Test 1 and Test 2

| Date | Backwash time hh:mm | Backwash flow L/m | Dissolved $O_3$ mg/L | Dose $O_3$ (mg $O_3$/kg C) | RLU | HPC |
|---|---|---|---|---|---|---|
| Test 1 | | | | | | |
| May 9, 2015 | 0:00 | 1100 | 0.00 | 0 | 481 | >200 |
| May 9, 2015 | 0:12 | 2350 | 0.50 | 7.5 | 68889 | 0 |
| May 9, 2015 | 0:25 | 2330 | 0.81 | 24.2 | 0 | 0 |
| May 9, 2015 | 0:50 | 2352 | 0.83 | 50.0 | 0 | 0 |
| May 9, 2015 | 1:15 | 2338 | 0.82 | 73.7 | 0 | 0 |
| May 9, 2015 | 1:40 | 2173 | 0.83 | 92.4 | 0 | 0 |
| May 9, 2015 | 2:05 | 2354 | 0.82 | 123.6 | 0 | 0 |
| May 9, 2015 | 2:30 | 2020 | 0.80 | 124.2 | 0 | 1 |
| Test 2 | | | | | | |
| May 15, 2015 | 0:00 | 300 | 0.00 | 0.0 | 88826 | >200 |
| May 15, 2015 | 0:07 | 1670 | 0.86 | 5.5 | 228110 | 6 |
| May 15, 2015 | 0:15 | 1505 | 0.62 | 7.2 | 71974 | 0 |
| May 15, 2015 | 0:30 | 1425 | 0.90 | 19.7 | 22025 | 0 |
| May 15, 2015 | 0:45 | 1650 | 1.02 | 38.8 | 0 | 0 |
| May 15, 2015 | 1:00 | 1500 | 1.14 | 52.6 | 23515 | 0 |
| May 15, 2015 | 1:15 | 1670 | 1.02 | 65.4 | 0 | 0 |
| May 15, 2015 | 1:30 | 1664 | 1.02 | 78.3 | 0 | 0 |

TABLE 2

IN against cumulative ozone dose following Tests 1 & 2

| Date | Cumulative Dose $O_3$ (mg/kg) | Iodine Index | Percent Increase |
|---|---|---|---|
| May 9, 2015 | 0 | 499 | |
| May 9, 2015 | 124.2 | 530 | 6% |
| May 15, 2015 | 124.2 | 374 | |
| May 15, 2015 | 202.4 | 422 | 13% |

Discussion of Results

As seen by the results above, a sufficiently low wt/wt dose of ozone has a significant effect on both sanitization and regeneration of activated carbon. The ability of the inventive method to regenerate the carbon with these low doses is surprisingly effective, as is the very quick sanitization effect. Sanitizing carbon within minutes is extremely attractive to many end users. Ten (10) minutes is a fairly typical backwash time for a GAC pressure filter, and sanitization control is often required weekly, whereas depletion of adsorptive capacity is typically significant only after a year. Thus, sanitization control with ozonated backwash keeps the adsorptive capacity high with the cumulative effect of short backwash cycles without significant interruption.

That this can be achieved in a much shorter time than normal makes more frequent sanitization desirable. Furthermore, the ozonation equipment needed to retrofit a current system would only be used a small portion of the total time. For this reason, when not being used for this purpose, the equipment can be used for clean-in-place (CIP) of other plant equipment, including biofilm elimination, complementing and partially replacing chemical cleaning, with powerful benefits to the user and the environment.

The novel ozone backwash step disclosed herein removes a surprising amount of adsorbed organics from spent activated carbon at a very low dose of ozone in comparison to backwash without ozone or other regeneration methods, and yields sanitized activated carbon with regenerated, increased adsorption capacity.

The novel process may be employed in any setting where activated carbon is used. It is particularly well-suited for on-site, in situ disinfection and regeneration of activated carbon that is used to adsorb organic contaminants. In particular, in water treatment facilities where high levels of organic loading are to be expected. In addition, although suitable for simultaneous disinfection (or sanitization) and regeneration, it should be understood that the invention does not require one or the other to occur. For example, the methods employed herein may result in disinfection only without any substantial regeneration and still remain within the scope of the invention (and vice versa).

Furthermore, economic estimates indicate the novel method disclosed herein for sanitizing and regenerating porous filter media should be substantially less expensive than current methods. For example, a steam regeneration cycle for the full scale filter costs about $6.35, mainly for the generation of steam; to regenerate with caustic soda would cost about $7.34, mainly for the chemical used and pumping and treatment cost for the rinse water; to regenerate with ozone costs about $1.03, mainly for electricity used in the production of ozone; pumping and treatment cost for the regular backwash cycle are omitted, as these are common to the three methods.

The regeneration and sanitization technique described herein is not limited to the described exemplary embodiments of a GAC filter, but can also be employed in the case of other porous medium adsorbers. Furthermore, it is not limited to beds through which the flow of the treated liquid, during operation of the filter, occurs from the top towards the bottom. Instead, the technique can also be employed with filters through which the liquid flows in the upward or radial direction. Finally, the method is not limited to the illustrated infeed configuration that supplies the ozone from the ozone generator to the backwash feed. Provided the requisite ozone doses, whether measured as ozone (wt)/filter media (wt) or alternatively as CT values, are achieved, the manner of generating, mixing, introducing or supplying the dissolved ozone does not have any influence upon the performance of the method.

In certain embodiments, the method steps of the invention can be carried out in addition to conventional backwashing operations, and said inventive steps can take place either before, during or after said conventional backwashing operation.

In certain embodiments, the system and method steps of the invention can be carried out in combination with, and in operational configuration, with primary filtration devices or other conventional water treatment methods, systems and devices.

GAC fixed bed adsorption filters may be used in combination (i.e. in sequence) with a primary filtration bed Embodiments of the invention include other forms of ozone generation in accordance with the current state of the art. By way of example only, in certain embodiments liquid ozone could be stored in cryogenic tanks and pass through evaporators to be dosed in the water as pure gaseous ozone.

The source of the feed water to be treated in accordance with this method is not critical. More specifically, the source may be ground water, industrial waste water streams, municipal waste water or sewage treatment effluents, surface water, potable drinking water, etc. However, the methods disclosed herein may be more beneficial for use in municipal potable water treatment versus industrial waste water treatment, which has higher levels of carbon loadings, heavy metals and hazardous contaminants. In particular, the method provides an in situ economical solution for small-scale water treatment systems in rural areas, where off-site regeneration facilities are far away, and/or other known techniques are not logistically feasible and/or affordable. The method is well-suited to be implemented on site, does not require spent carbon to be transported to a specialized facility for regeneration, and avoids the need for steam sanitization and its high energy consumption and waste. The method disclosed herein also has produced unexpected results in that past attempts to use ozone have shown that carbon destroys the ozone, thus preventing the ozone to reach deep into the bed.

CLAUSES

Embodiments of the present invention, include but are not limited to, the following:

1. A method for sanitizing a fixed bed of porous filter media employed in treating a water stream, wherein said fixed bed has a first flow direction during filtration, comprising the steps of:
    (a) mixing ozone with at least a portion of a water stream to produce an ozonated feed stream comprising a dissolved ozone solution;
    (b) introducing the dissolved ozone solution into said fixed bed at a second flow direction substantially different from the first flow direction;
    (c) contacting the porous filter media with the dissolved ozone solution for a predetermined time and in a concentration sufficient to sanitize said filter media;
    and wherein said contacting step is conducted at a predetermined minimum fluidization velocity for the filter media.
2. A method according to claim 1 wherein the dissolved ozone solution comprises 0.5 mg/L to 12 mg/L residual dissolved ozone when introduced into the fixed bed.
3. A method according to claim 1 wherein said filter media has a reduced adsorptive capacity prior to said contacting step, and a portion of said reduced adsorption capacity is restored by said contacting step.
4. A method according to claim 1 wherein the step of introducing the dissolved ozone solution comprises backwashing said filter media using the dissolved ozone feed stream.
5. A method according to claim 1 wherein said filter media comprises insoluble porous particles and the minimum fluidization velocity is a velocity sufficient to agitate said particles to provide repeated contact between the particles and the dissolved ozone.
6. A method according to claim 1 wherein the minimum fluidization velocity is a velocity sufficient to achieve a target bed expansion in the range of 20% to 60%.
7. A method according to claim 1 wherein the minimum fluidization velocity is a velocity sufficient to achieve a target bed expansion in the range of 35% to 60%.
8. A method according to claim 1 wherein the minimum fluidization velocity is a velocity sufficient to achieve a target bed expansion in the range of 20% to 35%.
9. A method according to claim 1 wherein the minimum fluidization velocity is a velocity sufficient to achieve a target bed expansion of 50%.
10. A method according to claim 1 wherein the minimum fluidization velocity is in the range of 5 to 60 m/h.
11. A method according to claim 1 wherein the minimum fluidization velocity is in the range of 20 m/h to 50 m/h.
12. The method according to claim 1 wherein the porous filter media are selected from the group consisting of granular activated carbon and pelletized activated carbon.
13. A method according to claim 1 wherein the porous filter media are selected from the group consisting of granular activated alumina, pelletized activated carbon, activated alumina, zeolite and synthetic magnesium silicate, and combinations thereof.
14. A method according to claim 1 wherein the ozone in the dissolved ozone solution is the only active treatment chemical.
15. A method according to claim 1 wherein the second flow direction is counter-current to the first flow direction.
16. A method according to claim 1 wherein the fixed bed converts to a fluidized bed.
17. A method according to claim 16 wherein the second flow direction is an upward vertical direction through the fluidized bed.
18. A method according to claim 1 wherein said contacting step is conducted at a temperature between 1° C. and 30° C.
19. A method according to claim 1 wherein said contacting step is conducted at a temperature between 20° C. and 25° C.
20. A method according to claim 1 wherein the concentration of the dissolved ozone solution in the ozonated feed stream that contacts the filter media is a residual ozone concentration, said residual concentration being produced by mixing a transferred ozone concentration of up to 20 mg/L with at least a portion of the feed water stream and prior to dilution with the remaining portion of the water stream.
21. A method according to claim 1 wherein said contacting step comprises a cumulative ozone dose in the range of 10 mg $O_3$/kg porous filter media to 300 mg $O_3$/kg porous filter media over the course of a single backwash cycle.
22. A method according to claim 21 wherein said contacting step comprises a cumulative ozone dose in the range of 20 mg $O_3$/kg porous filter media to 200 mg $O_3$/kg porous filter media over the course of a single backwash cycle.
23. A method according to claim 22 wherein said contacting step comprises a cumulative ozone dose in the range of 30 mg $O_3$/kg porous filter media to 100 mg $O_3$/kg porous filter media over the course of a single backwash cycle.
24. A method according to claim 21 wherein said contacting step comprises a cumulative ozone dose in the range of 160 mg $O_3$/kg porous filter media to 180 mg $O_3$/kg porous filter media over the course of a single backwash cycle.
25. A method according to claim 21 wherein said contacting step comprises a cumulative ozone dose of 10 mg $O_3$/kg porous filter media over the course of a single backwash cycle.
26. A method according to claim 1 wherein said contacting step comprises a cumulative ozone dose in the range of 1.0 g $O_3$/kg porous filter media to 30 g $O_3$/kg porous filter media over the course of a year.
27. A method according to claim 1 for disinfection, wherein the pH value of the ozonated inlet stream ranges from 5 to 7.
28. A method according to claim 1 for disinfection, wherein the pH value of the ozonated inlet stream ranges from 6 to 6.5.
29. A method according to claim 1 for disinfection, wherein the pH value of the ozonated inlet stream is 6.
30. A method according to claim 1 for oxidizing hazardous compounds retained by the filter media, wherein the pH value of the ozonated inlet stream ranges from 8 to 10, and is preferably 9.
31. A method according to claim 1 wherein said contacting step is maintained for a period of time sufficient to remove portions of contaminants adsorbed to the porous filter media.

32. A method according to claim 31 wherein said the contaminants are selected from the group comprising viruses, bacteria, protozoans, and other microorganisms.

33. A method according to claim 31 wherein said the contaminants include organic compounds.

34. The method according to claim 1 wherein microorganisms contained within said filter media are substantially eliminated.

35. A method according to claim 1 wherein said contacting step is 10 to 45 minutes.

36. A method according to claim 1 wherein said contacting step is 10 minutes.

37. A method according to claim 1 wherein said contacting step is 5 to 60 minutes.

38. A method according to claim 1 wherein said contacting step is 5 to 120 minutes.

39. A method according to claim 1 wherein the residual concentration of the dissolved ozone solution comprises about 1.5 mg/L ozone, and wherein said contacting step is 10 to 45 minutes, and is performed at a temperature of 1° C. to 30° C.

40. A method according to claim 1, additionally comprising a step, following said contacting step, of discharging backwash effluent from the filter bed to a waste drain for disposal, wherein said backwash effluent is depleted in ozone.

41. A method according to claim 1, additionally comprising a step, prior to said contacting step, of producing the dissolved ozone solution.

42. The method of claim 1 wherein the water stream is selected from the group consisting of municipal waste water, surface water, industrial waste water, industrial process water, groundwater, and drinking water.

43. A method of simultaneously sanitizing and regenerating a fixed bed filter containing porous particles and employed in filtering a water stream, wherein said fixed bed comprises a first flow direction during filtration, said method comprising the steps of:
   (a) mixing ozone with a portion of a purified water stream to produce a dissolved ozone solution;
   (b) initiating a backwash cycle by introducing the dissolved ozone solution into said fixed bed at a second flow direction opposite to that of the first flow direction;
   (c) filling said fixed bed with the dissolved ozone solution at a minimum flow rate sufficient to expand the fixed bed and create a fluidized bed, thereby agitating the particles contained within the fluidized bed and allowing the ozone to directly and repeatedly contact the porous particles with the dissolved ozone solution as the only active treatment chemical, and
   (d) discontinuing contacting said porous particles with the dissolved ozone solution.

44. A method according to claim 43 wherein said dissolved ozone solution filling the fixed bed in step (c) has a residual concentration in the range of 0.5 mg/L to 12 mg/L dissolved ozone.

45. A method according to claim 44 wherein said dissolved ozone solution filling the fixed bed in step (c) has a residual concentration in the range of 1.0 mg/L to 10 mg/L dissolved ozone.

46. A method according to claim 45 wherein said dissolved ozone solution filling the fixed bed in step (c) has a residual concentration in the range of 5.0 mg/L to 8 mg/L dissolved ozone.

47. A method according to claim 43 wherein said filling step (c) comprises a predetermined backwash velocity greater than a filtration velocity for the filter.

48. A method according to claim 43 wherein step (c) is carried out for a period of 10 to 45 minutes.

49. A method according to claim 43 further comprising a step of returning to filtration immediately following step (d).

50. A system for simultaneously sanitizing and regenerating exhausted activated carbon, comprising
   a vessel containing a fixed bed of porous filter media with a first flow direction for filtration;
   an ozone generator for producing ozone;
   a first backwash stream comprising purified water with a second flow direction different from said first flow direction;
   an ozone injector device operationally configured to inject ozone into at least a portion of said first backwash stream to produce an ozonated backwash stream with a predetermined residual ozone concentration; and
   a waste drain for disposal of and discharging backwash effluent from said fluidized bed, wherein said backwash effluent is depleted of dissolved ozone,
   wherein said system is configured to turn from a filtration mode to a backwash mode for backwashing said filter bed at the second flow direction using the ozonated backwash stream and at a minimum fluidization velocity sufficient to convert the fixed bed to a fluidized bed.

51. A system according to claim 50 wherein said vessel has a minimum freeboard of 35%.

52. A system according to claim 50 further comprising a pH adjustment device.

53. A system according to claim 50 wherein the backwash stream enters the vessel at a bottom portion of the vessel below the fixed bed, and said second flow direction is in an upward direction.

54. A system according to claim 50 wherein the amount of water required for sanitization is reduced.

55. A system according to claim 50 operationally configured to retrofit an existing water treatment system.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

As used herein, the terms "comprising," "has," "including," "containing," and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

All publications/references cited in this specification are herein incorporated by reference as if each individual publication were specifically and individually indicated to be incorporated by reference herein as though fully set forth.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

The invention claimed is:

1. A method for sanitizing an adsorption filter bed, wherein said filter bed comprises activated carbon and has a first flow direction during filtration, comprising the steps of:
    (a) mixing ozone with at least a portion of a water stream to produce an ozonated feed stream comprising a dissolved ozone solution comprising 0.5 mg/L to 12 mg/L residual dissolved ozone;
    (b) introducing the dissolved ozone solution into the activated carbon adsorption filter bed at a second flow direction substantially different from the first flow direction;
    (c) contacting the activated carbon with the dissolved ozone solution for a predetermined time and in a concentration sufficient to sanitize said activated carbon, wherein said contacting step is conducted at a predetermined minimum fluidization velocity sufficient to achieve a target bed expansion in the range of 35% to 60%.

2. A method according to claim 1 wherein the activated carbon adsorption filter bed has a reduced adsorptive capacity prior to said contacting step, and a portion of said reduced adsorption capacity is restored by said contacting step.

3. A method according to claim 1 wherein the step of introducing the dissolved ozone solution comprises backwashing the activated carbon adsorption filter bed using the dissolved ozone feed stream.

4. A method according to claim 1 wherein said activated carbon adsorption filter bed comprises insoluble particles of activated carbon and the minimum fluidization velocity is a velocity sufficient to agitate substantially all of the activated carbon particles in the filter bed and provide repeated contact between substantially all of the activated carbon particles and the dissolved ozone.

5. A method according to claim 4 wherein the insoluble particles of activated carbon are selected from the group comprising granular activated carbon and pelletized activated carbon.

6. A method according to claim 1 wherein the minimum fluidization velocity is a velocity sufficient to achieve a target bed expansion of 50%.

7. A method according to claim 1 wherein the minimum fluidization velocity is in the range of 5 m/h to 60 m/h.

8. A method according to claim 1 wherein the minimum fluidization velocity is in the range of 20 m/h to 50 m/h.

9. A method according to claim 1 wherein the second flow direction is counter-current to the first flow direction.

10. A method according to claim 1 wherein the filter bed converts to a fluidized bed.

11. A method according to claim 10 wherein the second flow direction is an upward vertical direction through the fluidized bed.

12. A method according to claim 1 wherein the concentration of the dissolved ozone solution in the ozonated feed stream that contacts the adsorption filter bed is a residual ozone concentration, said residual concentration being produced by mixing a transferred ozone concentration of up to 20 mg/L with at least a portion of the water stream and prior to dilution with the remaining portion of the water stream.

13. A method according to claim 1 wherein said contacting step comprises a cumulative ozone dose in the range of 10 mg $O_3$/kg porous filter media to 300 mg $O_3$/kg porous filter media over the course of a single backwash cycle.

14. A method according to claim 13 wherein said contacting step comprises a cumulative ozone dose in the range of 160 mg $O_3$/kg porous filter media to 180 mg $O_3$/kg porous filter media over the course of a single backwash cycle.

15. A method according to claim 1 wherein said contacting step comprises a cumulative ozone dose in the range of 1 g $O_3$/kg porous filter media to 30 g $O_3$/kg porous filter media over the course of a year.

16. A method according to claim 1 for disinfection, wherein the pH value of the ozonated feed stream ranges from 5 to 7.

17. A method according to claim 1 for oxidizing hazardous compounds retained by the activated carbon, wherein the pH value of the ozonated feed stream ranges from 8 to 10, and is preferably 9.

18. A method of simultaneously sanitizing and regenerating an adsorption filter bed containing insoluble particles of activated carbon, wherein said filter bed comprises a first flow direction with a target filtration velocity during filtration, said method comprising the steps of:
    (a) mixing ozone with a portion of a purified water stream to produce a dissolved ozone solution;
    (b) initiating a backwash cycle by introducing the dissolved ozone solution into the adsorption filter bed at a second flow direction opposite to that of the first flow direction, wherein the dissolved ozone solution has a residual concentration in the range of 0.5 mg/L to 12 mg/L dissolved ozone when introduced into the filter bed;
    (c) filling said filter bed with the dissolved ozone solution at a minimum flow rate sufficient to expand the filter bed and create a fluidized bed, thereby agitating the insoluble activated carbon particles contained within the fluidized bed and allowing the ozone to directly and repeatedly contact the activated carbon particles with the dissolved ozone solution as the only active treatment chemical;
    (d) discontinuing contacting the activated carbon particles with the dissolved ozone solution; and
    (e) initiating filtration immediately following step (d);
    wherein the filling step (c) comprises a target backwash velocity greater than the target filtration velocity and is carried out for a period of 10 to 45 minutes.

19. A method according to claim 18 wherein the insoluble particles of activated carbon are selected from the group comprising granular activated carbon and pelletized activated carbon.

* * * * *